United States Patent [19]

Weisser et al.

[11] 4,071,816
[45] Jan. 31, 1978

[54] MONITORING SUSPENSION STABILITY

[75] Inventors: Eugene P. Weisser, Verona, Pa.; G. Alan Osan, Marlton, N.J.; Edward P. Mailki, Lower Burrell, Pa.

[73] Assignee: ARCO Polymers, Inc., Philadelphia, Pa.

[21] Appl. No.: 726,372

[22] Filed: Sept. 24, 1976

Related U.S. Application Data

[62] Division of Ser. No. 630,484, Nov. 10, 1975, Pat. No. 4,007,319.

[51] Int. Cl.² ............................................. G01N 27/42
[52] U.S. Cl. ................................... 324/30 B; 204/293
[58] Field of Search .............. 204/292, 293; 324/30 B, 324/72.5

[56] References Cited

U.S. PATENT DOCUMENTS

| 1,592,979 | 7/1926 | Keeler | 324/30 B |
| 3,025,459 | 3/1962 | Eckfeldt | 324/30 B |

Primary Examiner—M. Tokar
Attorney, Agent, or Firm—Lewis J. Young

[57] ABSTRACT

A method for detecting impending failure of suspension during an aqueous suspension polymerization has been developed by continuous monitoring of the electrical conductivity of the suspension system. A sudden drop in conductance warns of failure of suspension in time to save the suspension by the addition of suspension stabilizers. A special conductivity cell has been developed to allow measurement of conductance during the course of the polymerization reaction.

1 Claim, 3 Drawing Figures

MONITORING SUSPENSION STABILITY

This is a divisional of application Ser. No. 630,484 filed 11/10/75 now U.S. Pat. No. 4,007,319.

BACKGROUND OF THE INVENTION

Polymer beads are often made by suspension polymerization in aqueous medium.

Sometimes, a "failure" of suspension occurs. When this happens, the hydrophobic materials tend to agglomerate and form a solid mass. This necessitates a shut-down of the equipment and a cleanout — often by chipping and hammering the mass of polymer from the interior of the reactors. This type of failure consumes time in cleaning and is costly, especially in lost production capacity.

If the suspension polymerization is run in an open reactor, the onset of suspension failure can be visually noted and the instant addition of stabilizers can be undertaken usually in time to avoid the failure.

However, if the suspension polymerization is run in a closed reactor, visual monitoring cannot be done. The need for a monitoring system to allow one to "see" the onset of suspension failure in closed reactors has been long recognized.

SUMMARY OF THE INVENTION

We have now found that such early warning of suspension failure can be obtained by monitoring the suspension system by measurement of the electrical conductance of the system. During the course of the polymerization, the conductance rises sharply to a maximum value and then levels off. If suspension starts to fail, the conductance of the system drops significantly. At this point, if additional stabilizer is added to the system, the conductance again increases to the original leveling off point — indicating a resumption of stable suspension conditions. This method has been shown to give warning 15 to 30 minutes in advance of the usual visual warning signs noted during open-reactor polymerization.

DETAILED DESCRIPTION

Figure 2:
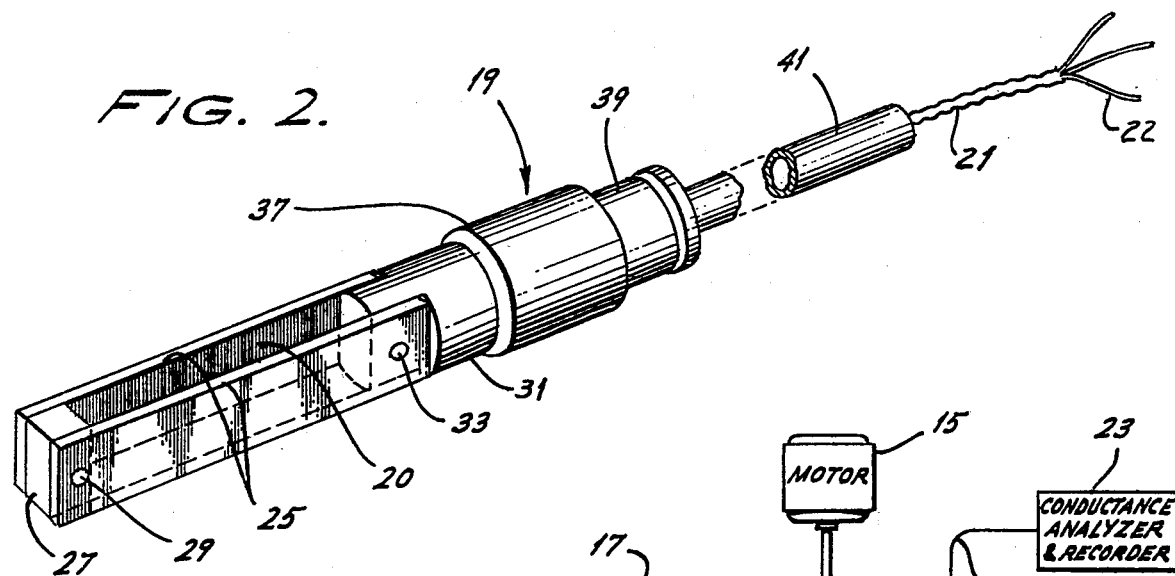
FIG. 2 is an enlarged view of a probe useful for measuring electrical conductance.

The process of the invention is applicable in the polymerization of monomers in aqueous suspension systems. The invention is especially applicable to suspension polymerization of vinyl aromatic monomers such as styrene, alpha-methylstyrene, mono- and di-chlorostyrene, vinyl naphthalene as well as the suspension copolymerization of vinyl aromatic monomers with such monomers as divinylbenzene, 2-ethylhexyl acrylate, diallyl esters of dibasic aliphatic or aromatic acids, butadiene, and polymers capable of further polymerization such as styrene-butadiene, styrene-isoprene, and polybutadiene rubbers. However, the use of other types of monomers, such as, for example, acrylonitrile, acrylate or methacrylate esters, vinyl chloride, vinylidene chloride and others which are suitable for aqueous suspension polymerization should be applicable in the current invention.

In a typical suspension polymerization, the monomers are mixed with water in a ratio of from 0.3 to 1.5 parts of monomer to 1 part of water. Vigorous agitation of the mixture causes the monomers to break up into beads or droplets of monomer dispersed in the water. As the monomers are converted to polymer within the droplets, the droplets become soft and sticky and, in the absence of sufficient agitation, or some aid to the maintenance of their individuality, the droplets may coalesce and form a sticky mass which sticks to the agitator or the reactor and causes suspension failure. To aid the suspension, it is customary to make use of suspending agents with or without an extender. The suspending agents may be protective colloids, such as water soluble polymers, polyvinyl alcohol, or hydroxyethyl cellulose, or certain inorganic salts, such as the difficultly water-soluble phosphates, carbonates or oxides. These suspending agents are used in amounts from 0.1 to 1.0 percent by weight based on the monomers used. The use of an extender to modify the bead particle size distribution of the product is common. Thus, Grim, in U.S. Pat. No. 2,673,194 teaches the use of sodium dodecylbenzene sulfonate, sodium tetradecyl sulfate, potassium stearate and long chain alkyl sulfonates; Hohenstein et al, in U.S. Pat. No. 2,652,392 used a water-soluble persulfate as extender for calcium phosphate suspending agent; and Wright, in U.S. Pat. Nos. 3,631,014 and 3,755,282, used sodium bisulfite and an unsaturated carboxylic acid, respectively. The extenders may be useful in amounts varying from 0.0003 to 0.05 percent by weight based on the total suspension.

The polymerizations are usually run with the aid of a free-radical producing catalyst dissolved in the monomers. The suitable catalyst, used in amounts between 0.05 and 1.0 percent by weight based on the monomers, may be of the oil-soluble peroxide type, such as benzoyl peroxide, lauroyl peroxide, t-butyl perbenzoate, and mixtures of various peroxides, or of the azo-type, such as azobisisobutyronitrile.

The polymerization may be carried out at temperatures below 95° C until the polymer beads have been formed at, for example, about 60% conversion of monomers to polymers. The final 40% conversion may be carried out at the same temperature as in the method of Grim, U.S. Pat. No. 2,673,194, or at temperatures as high as 150° C as in the method of D'Alelio, U.S. Pat. No. 2,692,260.

Figure 1:
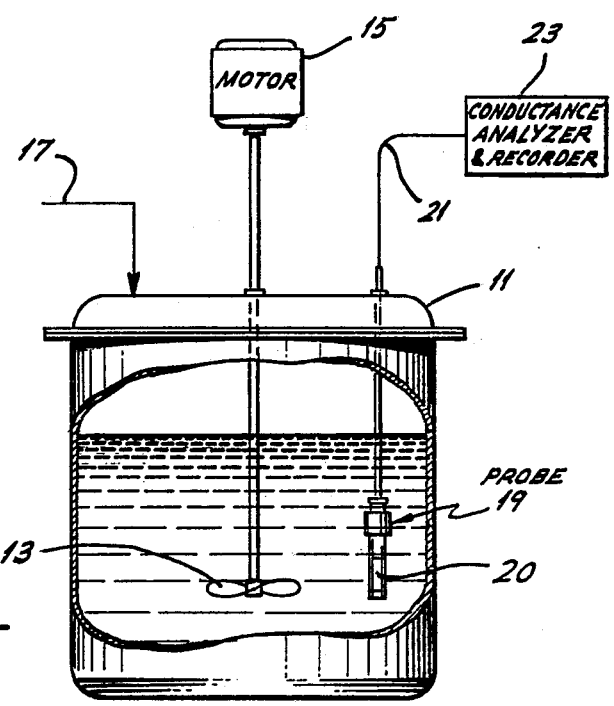
FIG. 1 is a schematic showing the reactor setup and the location of the probe in relation to the reactor.

The apparatus used in the present invention is shown in FIG. 1. The reactor 11 is fitted with a stirrer, 13, which is driven by a motor, 15, to provide sufficient agitation to maintain the system in suspension. All ingredients are added through a line, 17. A probe, 19, is positioned in the reactor such that the interelectrode opening, 20, between the flat surfaces of the electrodes is parallel to the sides of the reactor. The probe is mounted so that the electrodes are about midway between the bottom of the reactor and the surfaces of the suspension. The lead wires, or cable, 21, is connected to the terminals of the conductivity analyzer, 23. The conductance may be read directly from a meter or recorded continuously on a line recorder.

The exact electrical conductance of the system need not be measured, so long as the measurements are relative to one another and made often enough to insure a good indication of the falling off point. This may be accomplished by using a continuous recorder, as shown in FIG. 1, by using a multiple point recorder, or by manual measurement at time intervals, for example, every 10 minutes.

The conductivity cell, or probe, used in the present invention was developed to overcome disadvantages found in commercially available probes. Thus, commercially available probes are limited in the temperature ranges usable, the pressure ranges usable, and the length of time they are usable without becoming fouled with polymer buildup.

Temperature affects the usual probes by melting polyethylene coatings from around the coaxial cables causing shorts in the system, by blistering Teflon coatings off of the electrodes, and by causing distortion of the cell housings when they are made of polystyrene. Polystyrene cell housings are also subject to solvent attack from styrene polymerization systems.

Pressure affects most of the above probes also, probably by causing increased temperature in the system.

Commercially available probes usually have a cell housing which interrupts the flow of suspension through the electrodes and allows polymer to build up on the surface of the electrode. The conductance readings are thereby interferred with.

The probe shown in FIG. 2 has overcome all of these difficulties. The stainless steel electrodes, 25, have highly polished, flat, rectangular surfaces, 6-5/18 inches high by 1½ inches wide and 3/16 inch thick. The electrodes are rigidly spaced apart about 7/8 inch and are parallel to one another, thus forming an inter-electrode space, 20, through which the fluid to be measured can flow freely. A Teflon spacer, 27, is fastened between the bottom of the electrodes by screws, 29, while a second Teflon spacer, 31 is fastened between the top of the electrodes by screws 33. The two spacers 27 and 31 are placed such that 5½ inches of the electrode plates is exposed to the suspension to be measured. The second spacer, 31, is securely fastened inside of a pipe coupling, 37. Each electrode is fastened for example by soldering, to a lead from a Teflon coated coaxial cable, 21, leading from the electrodes up through an exit pipe, 41, to the outisde of the closed reactor. The third lead, 22, shown exiting the pipe, 41, is the shield lead from the coaxial cable. The other end of the coaxial cable is connected to the terminals of a conductivity analyzer, 23. The leads are sealed inside a 1½ inch pipe coupling, 37, which is then connected to the exit pipe, 41, through a reducing bushing, 39. The entire area of connection of the electrode plates to the coaxial cable, including the pipe coupling, 37, is embedded in an epoxy-type resin capable of withstanding temperatures of at least 150° C at pressures of up to 150 psig to insure against attack of the cable by the suspension medium at the temperature and pressure of the reaction. The pipe, 41, exits the lid of the reactor through a suitable opening which can be closed to pressure by a pipe bushing having, for example, a suitable pressure fitting through which the coaxial cable pipe can exit. The probe's parallel plates are mounted at a level such that they extend into the middle of the suspension. The probe is mounted so that the opening between the parallel plates is itself parallel to the inner walls of the reactor. This allows the suspension medium to flow unimpaired between the plates of the probe and prevents polymer buildup on the plates. The probe is, thus capable of operation at temperatures as high as 150° C at pressures of 150 psig and is not fouled by the accumulation of polymer on the electrodes because of the washing action of the suspension passing through the interelectrode space.

The invention is illustrated, but not limited by, the following examples, wherein all parts are parts by weight.

EXAMPLE I

Figure 3:
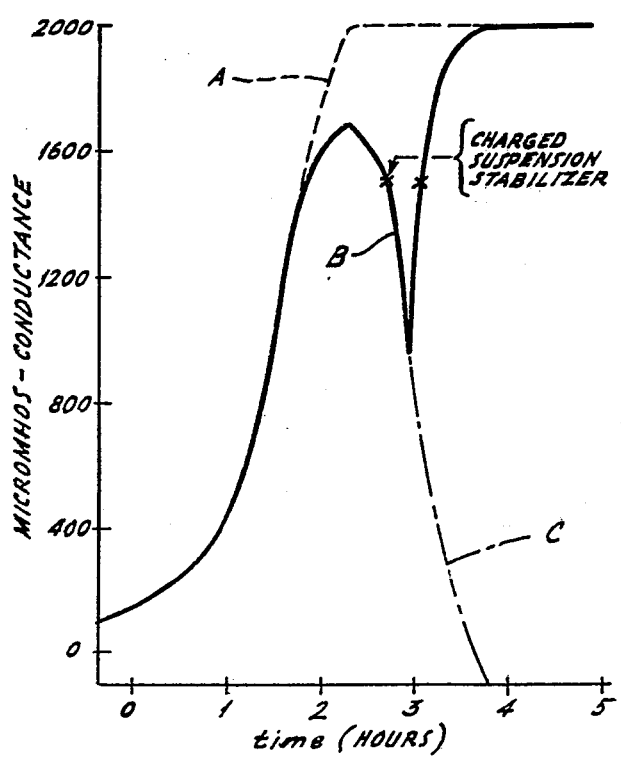
FIG. 3 is a graph of the electrical conductance versus time in a typical suspension polymerization and in a "failing" suspension polymerization.

To a reactor equipped with two-four bladed impellers, there was added 42 parts of water containing 0.1316 parts of the suspending system consisting of 0.131 parts of tricalcium phosphate and 0.0006 parts of sodium dodecylbenzene sulfonate and 58 parts of styrene having dissolved therein 0.171 parts of the catalyst comprising 0.145 parts benzoyl peroxide and 0.026 parts t-butyl perbenzoate. A conductivity cell, as described in FIG. 2, was inserted through the top of the reactor and mounted about midway in the suspension medium, with the electrode plates parallel to the sides of the reactor. The suspension was agitated at 68 rpm., and heated to 90° C over 1.0 hour. The suspension was maintained at 90° C for 6 hours. The conductance of the system was measured continuously using the probe of FIG. 2 as indicated in the specification and a Series 25 Analyzer sold by Aquatronics, Inc. of Philadelphia, Pa. The results of the measurements are shown in FIG. 3, line A. It will be seen in FIG. 3, that the electrical conductance rose with time up to a maximum of 2000 micromhos at 2 and a half hours and then remained at that level throughout the time. This suspension did not "fail" and hence no change in conductance occurred. The suspension was then cooled and acidified with hydrochloric acid to a pH of about 1.0 to dissolve the phosphate. The beads were separated by centrifuge, washed with water and air dried. This example illustrates the type of conductance vs. time curve obtained during a normal, non-failing, suspension polymerization.

EXAMPLE II

This example illustrates the type of conductance vs. time curve obtained during a suspension polymerization which starts to fail, then recovers on addition of more suspending agent. (See FIG. 3, curve B). The reactor was charged as in Example I and the conductivity cell mounted as before. The mixture was agitated and heated to 90° C as in Example I. After 2 hours, the electrical conductance started to level off and at 2½ hours had peaked at 1700 micomhos. At 2 hours 50 minutes, the conductance had definitely fallen to 1400 micromhos, and a mixture of 0.0260 parts tricalcium phosphate and 0.003 parts sodium dodecylbenzene sulfonate was added to the suspension. The conductance was noted to continue falling to about 950 micromhos at 3 hours, then climb rapidly to a maximum of 2000 micromhos where the conductance leveled off as in a normal run. It was thus shown that the measurement of electrical conductance of the suspension system gave early enough warning of impending suspension failure to enable the suspension to be re-stabilized.

A similar suspension run is shown in FIG. 3, curve C, wherein no additional stabilizers were added and the suspension failed completely. The resulting product was agglomerated into a mass, sometimes referred to as a "lollipop", which stopped the agitator and required extensive cleanout of the reactor before a new charge could be added.

We claim:

1. A electrical conductivity cell consisting of a first and second stainless steel electrode each having a highly polished flat, rectangular surface and said electrodes being rigidly spaced apart with said rectangular surfaces parallel to each other to form an interelectrode space through which a liquid to be measured containing soft and sticky polymer droplets may pass freely, without allowing polymer to build up on the surfaces of the electrodes, said spacing being kept rigidly uniform by a first non-electrically conducting spacer at the bottom of the electrodes and a second non-electrically conducting spacer at the top of the electrodes, said top spacer being fastened to a pipe coupling and through a reducing bushing to an exit pipe which is long enough to exit any reactor in which the cell is used while the cell plates are immersed into the liquid to be measured; each of said electrodes being connected inside the pipe coupling to an insulated wire; said wires being carried outside of the reactor inside the exit pipe; and said connections and said pipe coupling being completely embedded by an epoxy resin capable of withstanding temperatures of at least 150° C at up to 150 psig pressure; said cell having no cell housing around the electrodes.

* * * * *